Figure 1:
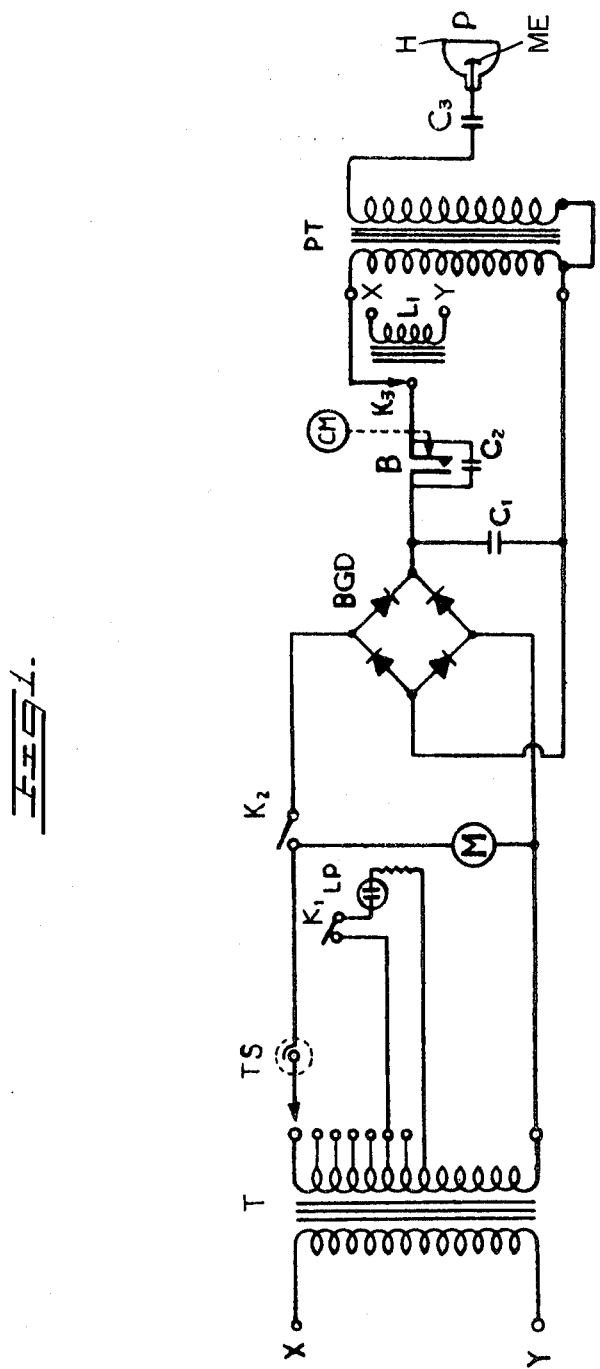

United States Patent [19]

Kim et al.

[11] 4,088,137

[45] May 9, 1978

[54] ELECTRON IRRADIATOR

[76] Inventors: In Su Kim, 54-1, 2-ka, Myong-dong, Chung-ku, Seoul; Bong Suk Lee, 407-10, Sinlim-dong, Kwanak-ku, Seoul, both of Korea

[21] Appl. No.: 736,229

[22] Filed: Oct. 27, 1976

[30] Foreign Application Priority Data

Oct. 28, 1975 Korea .................................. 2311

[51] Int. Cl.$^2$ ............................................. A61N 1/00
[52] U.S. Cl. ................................................. 128/419 N
[58] Field of Search .................... 128/24.1, 24.4, 24.5, 128/172.1, 419 N

[56] References Cited

U.S. PATENT DOCUMENTS 2,589,613  3/1952  Hicks ............................. 128/419 X
3,678,337  7/1972  Grauvogel ..................... 128/419 N

FOREIGN PATENT DOCUMENTS 1,063,293  8/1959  Germany ......................... 128/419 N Primary Examiner—Lawrence W. Trapp
Attorney, Agent, or Firm—Cameron, Kerkam, Sutton, Stowell & Stowell

[57] ABSTRACT

An electron irradiator for supplying electrons to the human body includes a discharging pole for application to the body and a power transformer connected to a D.C. source via an interrupter, the secondary of the power transformer being connected to the discharging pole via a condenser which charges and discharges at the repetition rate of the interrupter whereby the electron space discharge of the discharging pole, when applied to the human body, supplies electrons to the body.

4 Claims, 2 Drawing Figures

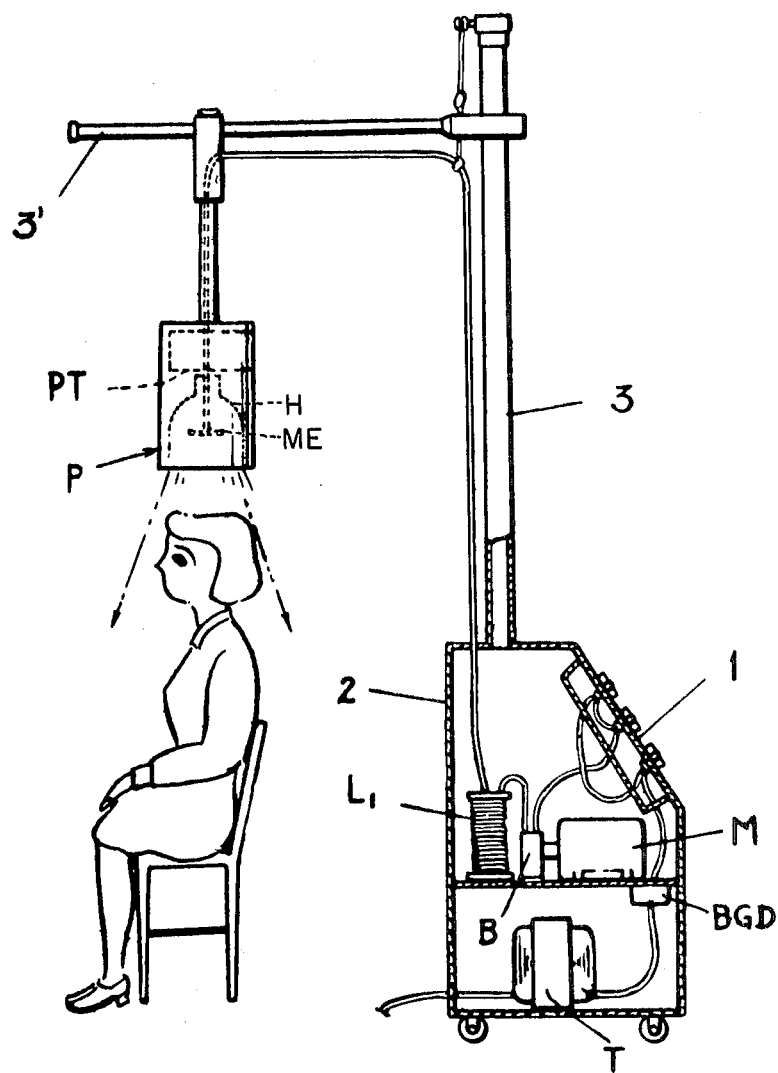

ELECTRON IRRADIATOR

The ion generator of the present invention is an improvement on the device disclosed in the copending application of In Su Kim, Ser. No. 596,164, filed July 15, 1975, now U.S. Pat. No. 4,010,742 dated Mar. 8, 1977, and produces and emits electrons for supplying the human body without producing any measurable amount of ozone gas, X-rays, gamma or microwave emissions that would be considered harmful to any form of biological life, including human.

Traditional physical therapies, such as X-ray, gamma-ray, ultraviolet and infrared ray radiation, have been applied to the human body, but were locally applied to destroy and/or bactericide malignant cells. Although these therapies may locally destroy or bactericide malignant cells, they have caused radiological damage on cells and tissue as side effects, and, and in extreme cases, chromosomes became abnormal or genes suffered from mutation. In contrast to these known physical therapies, the present invention extracts and emits only negatrons which are supplied to the cellular tissue of the human body without causing any side effects so that the human body may charge active energy into itself.

As it is generally well known that electrons play an important role in the human body, the reason why electrons are required in the human body is due to the fact that the electron is the foundation of vital electric current as the base of metabolism. For example, the shortage of electrons in the human body means a shortage of vital electric current, and is considered a shortage of energy in the human body. The electron requirement of the human body is considered to be the electrons generated from the energy obtained in the oxidation process to produce adenosine diphosphate from adenosine triphosphate produced in the disassimilation and synthesization process of ingested food, nutrients, vitamins, etc. The thus generated electrons charge mitochondria in cells through a transfer system and mitochondria supplies vital electric current required for the mechanism of human physical functions. Such electrons are supplied by ingested food and nutrients. It is generally known that in case internal organ function is not normal due to disease, fatigue or other cause, sufficient electrons are not obtained from ingested food and nutrients and overall physical balance is not maintained; then various symptoms appear and good health is difficult to be maintained.

The device of the present invention supplies electrons through the human body surface, supplements the shortage of electrons and enables a human being to maintain his good health.

Referring now to the drawings:

FIG. 1 is a diagram of the electrical circuit of the electron irradiator of the present invention; and FIG. 2 is a side elevation, partly in section, of an electron irradiator illustrating how the device of FIG. 1 is used to supply electrons to a human being.

Referring now to FIG. 1, the primary coil of transformer T is connected at terminals X,Y to a source of 100-120 volts A.C. The extremities of the secondary coil of transformer T are connected via a bridged rectifier BGD to the primary coil of an output power transformer PT, a smoothing condenser $C_1$ being connected across the leads to the outut power transformer, whereby a steady 6-25 volts of D.C. is obtained from the power source X,Y. The lead from one end of the secondary coil of transformer T to the bridge rectifier BGD includes a timer switch TS, and a voltmeter M is connected across the two leads from the upper and lower ends of the secondary coil of transformer T. A subsidiary circuit connected to taps on the secondary coil of transformer T includes a power switch $K_1$ and a neon indicating lamp LP. The lead between the upper end of the primary coil of output power transformer PT and one of the output terminals of the bridged rectifier BGD includes an interrupter B bridged by a condenser $C_2$ and driven by a cycle motor or transistor chopper CM, and a switch $K_3$ which is a manually operated motor control switch. $L_1$ is a magnetic pickup coil which attracts electrons by magnetic effect.

One end of the secondary coil of output power transformer PT is connected via a condenser $C_3$ to the discharging pole P of the apparatus, while the opposite end of the secondary coil is connected to the other output terminal of the bridged rectifier BGD. The discharging pole P consists of a multiple electrode ME made of fine stainless steel gauze, mounted within a hood H of non-conductive material, and, as will be evident from FIG. 1, is ungrounded. With the circuit shown in FIG. 1, the voltage induced in the primary coil of output power transformer PT by interrupter B charges and discharges the secondary coil of said transformer and produces a negative electron space discharge through one side pole of condenser $C_3$ by a charging and discharging action.

As shown in FIG. 2, the electronic circuit of FIG. 1 is housed in a casing 2 having a regulating panel 1, while the output power transformer PT, the condenser $C_3$ and the electron discharging pole P are suspended from a horizontal bar 3' connected to an upwardly extending support 3 mounted on top of casing 2. With this construction, electrons can be discharged to any part of the human body at a proper distance from the discharging pole P. Power is supplied to the discharging pole and the desired cycle is obtained by operating cycle motor or transistor chopper CM and interrupter B, the supply of D.C. current to the primary coil of output power transformer PT repeats on and off so that the voltage induced at the secondary coil of the transformer is charged to condenser $C_3$. If the phase of the induced current at the secondary coil of output transformer PT changes by the on and off operation of interrupter B, the electron charge in condenser $C_3$ produces a space discharge through discharging pole P and supplies the human body with electrons.

The device of the present invention may supply the human body with electrons because the human body electronically is a semi-conductor, and therefore readily absorbs electrons through cells and charges electrons into itself, and the charged electrons are supplied as energy required for human physical functions to various parts of the human body through the transfer system. Consequently, a shortage of electrons, resulting from disease or other cause, may be more quickly supplemented by electrons supplied from the outside, than by ingested food and nutrients, whereupon physical balance is recovered, disease can be treated and good health can be maintained.

In the device of the present invention, the frequency of the interrupter is controlled by the cycle motor or transistor chopper; consequently the frequency is always stable, there are no side effects such as radioactive damage, and disease can be treated in a short period of time.

What is claimed is:

1. An electron irradiator for supplying electrons to the human body comprising an ungrounded electron discharging pole adapted to be brought into proximity to a human body, a source of direct current, a power transformer connected to said D.C. source, an interrupter in the connection between the power transformer and the D.C. source, means for closing and opening the contacts of said interrupter at a predetermined repetition rate, the secondary of said power transformer being connected to the discharge pole, a condenser in the connection between the secondary of the said power transformer and said discharging pole which charges and discharges at the repetition rate of the interrupter, whereby the electron space discharge of the discharging pole, when brought adjacent to the human body, supplies electrons to the body.

2. An electron irradiator as claimed in claim 1 wherein said discharging pole comprises a multiple electrode housed within a hood of non-conductive material adapted to be brought into proximity to a human body to be treated.

3. An electron irradiator as defined in claim 2 wherein said multiple electrons comprises a body of fine stainless steel gauze.

4. An electron irradiator as claimed in claim 1 wherein said D.C. source comprises a bridged rectifier connected to a source of alternating current, and said interrupter includes a cycle motor for driving the interrupter at a predetermined repetition rate, and wherein the voltage induced in the secondary coil of said power transformer by the on-and-off energization of said primary coil charges and discharges said condenser and thereby produces an electron space discharge by said discharging pole.

* * * * *